US010687441B2

(12) United States Patent
Parnes et al.

(10) Patent No.: US 10,687,441 B2
(45) Date of Patent: Jun. 16, 2020

(54) VACUUM-BASED THERMAL MANAGEMENT SYSTEM

(71) Applicant: Zuta-Core Ltd., Moshav Sde-Avraham (IL)

(72) Inventors: Tal Parnes, Kfar Saba (IL); Nahshon Eadelson, Moshav Sde-Avraham (IL)

(73) Assignee: ZUTA-CORE LTD., Moshav Sde-Avraham (IL)

( * ) Notice: Subject to any disclaimer, the term of this patent is extended or adjusted under 35 U.S.C. 154(b) by 0 days.

(21) Appl. No.: 16/020,039

(22) Filed: Jun. 27, 2018

(65) Prior Publication Data

US 2018/0317344 A1 Nov. 1, 2018

Related U.S. Application Data

(63) Continuation of application No. PCT/IL2016/051384, filed on Dec. 27, 2016.
(Continued)

(51) Int. Cl.
*H05K 7/20* (2006.01)
*G06F 1/20* (2006.01)
(Continued)

(52) U.S. Cl.
CPC ....... *H05K 7/20381* (2013.01); *A61F 7/0085* (2013.01); *A61F 7/02* (2013.01);
(Continued)

(58) Field of Classification Search
CPC . H01L 23/427; H01L 23/473; F28D 15/0266; F28D 15/02; F28D 15/00;
(Continued)

(56) References Cited

U.S. PATENT DOCUMENTS

| 4,154,296 A | 5/1979 | Fijas |
| 5,186,242 A * | 2/1993 | Adachi ............... B60H 1/3202 165/104.27 |

(Continued)

FOREIGN PATENT DOCUMENTS

| CN | 104534710 A | 4/2015 |
| DE | 19918582 A1 | 2/2000 |

(Continued)

OTHER PUBLICATIONS

PCT/IL2018/050809 International Search Report and Written Opinion dated Dec. 12, 2018.
(Continued)

*Primary Examiner* — Adam B Dravininkas

(57) ABSTRACT

A thermal management system and method are presented for cooling an entity. The system comprises: a closed loop fluid flow line for flow of a coolant while being transferred in between its liquid and gas phases; at least one cooling zone located within the flow line and comprising at least one cooling interface; a vacuum generator unit operable for creating and maintaining vacuum condition at the cooling zone to thereby reduce evaporation temperature of the coolant located in the cooling zone; and a condensation zone spaced apart from the cooling interface downstream thereof with respect to a direction of the coolant flow from the cooling zone along the closed loop path wherein the coolant is condensed to liquid phase.

19 Claims, 8 Drawing Sheets

Related U.S. Application Data

(60) Provisional application No. 62/272,290, filed on Dec. 29, 2015.

(51) Int. Cl.

| | | |
|---|---|---|
| *A61F 7/02* | (2006.01) | |
| *A61F 7/00* | (2006.01) | |
| *F28D 15/02* | (2006.01) | |
| *F28D 15/06* | (2006.01) | |
| *F28D 15/00* | (2006.01) | |

(52) U.S. Cl.
CPC ......... *F28D 15/0266* (2013.01); *F28D 15/06* (2013.01); *G06F 1/20* (2013.01); *H05K 7/208* (2013.01); *H05K 7/20309* (2013.01); *A61F 2007/0002* (2013.01); *A61F 2007/0007* (2013.01); *A61F 2007/0054* (2013.01); *A61F 2007/0056* (2013.01); *A61F 2007/0058* (2013.01); *A61F 2007/0078* (2013.01); *A61F 2007/0087* (2013.01); *A61F 2007/0228* (2013.01); *A61F 2007/0233* (2013.01); *A61F 2007/0292* (2013.01); *F28D 15/00* (2013.01)

(58) Field of Classification Search
CPC .. F28D 15/0233; F28D 15/0275; F28D 15/04; F28D 15/046; F28D 21/0015
See application file for complete search history.

(56) References Cited

U.S. PATENT DOCUMENTS

| | | | |
|---|---|---|---|
| 5,201,365 A | 4/1993 | Sigel | |
| 5,317,905 A | 6/1994 | Johnson | |
| 5,507,150 A * | 4/1996 | Weber .................... | B64D 13/00 62/100 |
| 6,673,594 B1 | 1/2004 | Owen et al. | |
| 9,301,557 B1 * | 4/2016 | Santos .................... | B32B 15/20 |
| 9,848,509 B2 * | 12/2017 | Shedd ................ | H05K 7/20327 |
| 2004/0240178 A1 * | 12/2004 | Kim .................... | F28D 15/0233 361/695 |
| 2006/0065386 A1 | 3/2006 | Alam | |
| 2007/0256824 A1 | 11/2007 | Kim et al. | |
| 2008/0030956 A1 * | 2/2008 | Silverstein .......... | F28D 15/0266 361/700 |
| 2008/0106865 A1 | 5/2008 | Luo | |
| 2008/0142053 A1 * | 6/2008 | O'Donnell .......... | B01D 19/0036 134/30 |
| 2009/0183857 A1 | 7/2009 | Pierce et al. | |
| 2010/0328882 A1 * | 12/2010 | Campbell ............. | H01L 23/427 361/689 |
| 2011/0277967 A1 * | 11/2011 | Fried ................... | F28D 15/0266 165/104.26 |
| 2012/0153514 A1 | 6/2012 | Baxter et al. | |
| 2012/0324933 A1 | 12/2012 | Louvar et al. | |
| 2013/0180689 A1 | 7/2013 | Boening | |
| 2014/0216688 A1 | 8/2014 | Shelnutt et al. | |
| 2015/0076241 A1 * | 3/2015 | Zhadanovsky ......... | F01K 17/02 237/9 R |
| 2015/0189796 A1 * | 7/2015 | Shedd .................... | F25B 41/00 361/699 |
| 2015/0351290 A1 | 12/2015 | Shedd et al. | |
| 2016/0330873 A1 | 11/2016 | Farshchian et al. | |

FOREIGN PATENT DOCUMENTS

| | | |
|---|---|---|
| DE | 102005021154 A1 | 11/2006 |
| DE | 102011081886 A1 | 2/2013 |
| EP | 0666214 A1 | 8/1995 |
| GB | 2405688 A | 3/2005 |
| WO | 2009021328 A1 | 2/2009 |
| WO | WO-2009141282 A2 | 11/2009 |
| WO | WO-2017115359 A1 | 7/2017 |
| WO | WO-2018167773 A1 | 9/2018 |
| WO | WO-2019021273 | 1/2019 |

OTHER PUBLICATIONS

PCT/IL2016/051384 International Search Report and Written Opinion dated Apr. 2, 2017.
PCT/IL2018/050280 International Search Report and Written Opinion dated Jun. 20, 2018.

* cited by examiner

VACUUM-BASED THERMAL MANAGEMENT SYSTEM

CROSS-REFERENCE

This Application is a continuation of International Application No. PCT/IL2016/051384, filed on Dec. 27, 2016, which claims priority to U.S. Provisional Application No. 62/272,290, filed on Dec. 29, 2015, both of which are incorporated herein by reference in their entireties.

TECHNOLOGICAL FIELD

The present disclosure relates to a thermal management system, more particular to a vacuum-based cooling system.

BACKGROUND

One of the major problems in the electronics field is increased heat generation as computing performance increases. The trend toward ever increasing heat dissipation in microprocessor and amplifier based systems, such as those housed in telecommunication cabinets and Cloud Computing centers, is becoming increasingly critical to the electronics industry. Thus, finding effective thermal solutions is a major constraint for the reduction of system cost, time-to-market and performance, three governing factors between success and failure in commercial electronics development and sales.

The problems caused by the increasing heat dissipation are further compounded by the industry trend toward system miniaturization-one of the main methodologies of the electronics industry to satisfy the increasing market demand for faster, smaller, lighter and cheaper electronic devices. The result of this miniaturization is increasing heat fluxes. Also, non-uniform heat flux distribution in electronics may result in peak heat fluxes in excess of 5× the average heat flux over the entire semiconductor chip surface. Under such conditions, integrating advanced heat-spreading and heat-reducing mechanisms into the semiconductor chip are essential. In addition, several refrigeration systems were developed for cooling the entire electronic system or just the heat-generating components therein.

Extensive efforts in the areas of heat sink optimization (including the use of heat pipes) and interface materials development in the past, have resulted in the significant reduction of sink-to-air and package-to-sink thermal resistances. However, the reduction of these two thermal resistances has now begun to approach the physical and thermodynamic limitations of the materials. In addition, prior art thermal transfer approaches, such as the use of AlSiC, CuW and diamond as semiconductor package lid and interface materials, have become inadequate for handling increasing heat dissipation requirements.

Successful cooling technologies must deal with thermal issues at the device, device cluster, printed wiring board, subassembly, and cabinet or rack levels, all of which are within the original equipment manufacturers' (OEM's) products. Many times, the problem is further complicated by the fact that the thermal solution is an "after thought" for the OEM. A new equipment design may utilize the latest software or implement the fastest new semiconductor technology, but the thermal management architecture is generally relegated to the "later phases" of the new product design. The thermal management issues, associated with a designed electronic system, are often solved by the expedient of a secondary cooling or refrigeration system that is arranged in tandem with the electronics system. Indeed, according to some known techniques CPUs' firmware comprises a code embedded therein that prevents the processor approaching its TDP (Thermal Design Point) and thus limits its performance to a significantly lower level than its maximized design level. However, in some other techniques, the CPU utilizes an Extended Frequency Range (XFR) feature, which automatically overclocks chips to their maximum potential, based entirely on how good the cooling is.

Further, many techniques for transporting live organs, tissues, pharmaceuticals or any other entity, component or ingredient needed to be cooled during transport, have been developed. For example, U.S. Pat. No. 6,673,594 describes an organ transport device having a perfusion capability. However, most devices either use cooling elements such as dry ice or require large scale refrigerating means that consume large amount of electricity and takes up a lot of space. In addition, standard active thermal management systems involve high pressure environment therein, which require special piping, connectors and sealants, which might burst at ambient pressure lower than 1 atm., such as during flight.

GENERAL DESCRIPTION

There is a need in the art for a high performance, cost effective, reliable thermal management system for use with heat-generating electronic systems (such as high performance electronic systems), as well as for simple and effective transportation of any object that needs to be stored and transported under cooling conditions, even by non-equalized flight.

Thus, there is a need in the art to provide a novel approach for cooling various entities, to provide an active cooling interface of a desirably low temperature with reduced dependence on the surrounding conditions.

The present disclosure concerns a novel thermal management system and method for cooling an entity. The system comprises a closed loop flow line for circulation of coolant therethrough and periodically interacting with a cooling interface, wherein the coolant is transferred (e.g. periodically or continuously) in between its liquid and gas phases while in the cooling interface. Thus, the coolant flows in a closed loop, absorbing heat through the phase change thereof from liquid to gas, in a cooling zone having an integral cooling interface, to thereby absorb heat from the entity to be cooled and dissipating it to the environment, typically through a coolant condensation. Thus, the coolant absorbs heat by the principle of latent heat. To this end, an active vacuum generator is used for applying, and maintaining by demand, partial vacuum in the cooling zone and thus reducing the boiling temperature of the coolant. The coolant then boils at a relatively low temperature, proportionally depending on the low pressure that is applied, absorbs the heat from its surrounding via latent heat and thereby reduces the temperature of the cooling zone, the coolant and thus the cooling interface. The entity to be cooled is located in a close vicinity or in direct contact with the cooling interface having a heat exchange therewith to reduce or maintain the entity temperature.

The cooling system of the invention thus enables (i) obtaining a high ratio of working volume to sealing surface, (ii) eliminating or at least significantly reducing the need for pressure protecting measures such as metal pipes, special connectors and valves, etc., and (iii) obtaining cooling to desirably low temperatures substantially independent on the surrounding conditions.

Thus, according to one broad aspect of the invention, it provides a thermal management system for cooling an entity comprising (i) a closed loop fluid flow line for flow of a coolant while being transferred in between its liquid and gas phases, (ii) at least one cooling zone located within said flow line and comprising at least one cooling interface and; (iii) a vacuum generator unit operable for creating and maintaining vacuum condition at the cooling zone to thereby reducing evaporation temperature of said coolant located in the cooling zone, (iv) a condensation zone spaced apart from the cooling zone downstream thereof with respect to a direction of the coolant flow from the cooling zone along said closed loop path wherein said coolant is condensed to liquid phase.

In the description below the thermal management system is at times referred to as a cooling system.

In some embodiments of the cooling system the operation of the vacuum generator and configuration of the flow line provide the reduced evaporation temperature of the coolant at said cooling interface permitting the cooling interface to be cooled to a desired temperature via latent heat, and condensation of coolant vapor at said condensation zone.

In certain embodiments of the cooling system, the closed loop flow line is configured to provide a pressure difference between different zones along the closed loop path to allow absorption of heat through evaporation of the coolant by applying partial vacuum, and emission of heat in different locations, having higher pressure, along the flow line.

In some embodiments of the cooling system, the flow line comprises at least one restriction mechanism comprising at least one of the following: an orifice, a one-directional valve, and a varying cross section of said closed loop flow line; said at least one restriction mechanism providing said pressure difference between the different zones.

In certain embodiments of the cooling system, the cooling interface is in direct contact with said entity to be cooled, the system thereby providing Direct Contact Liquid Cooling (DCLC) of said entity. Direct contact in this application consider also a contact of the cooling interface with a mediator material in a direct contact with the entity to be cooled. Preferably, such mediator is having a high heat conductivity.

In some embodiments of the cooling system, the condensation zone is defined by a region of the flow line exposed to surrounding pressure. In this specific embodiment the coolant is utilized in the system usually characterized to undergo a condensation under the surrounding pressure, namely atmospheric pressure, in the ambient pressure temperature.

In some embodiments of the cooling system, the condensation zone is defined by a condenser unit to thereby provide pressure in the condenser unit increased above surrounding pressure.

In certain embodiments of the cooling system, the cooling interface is made of a material composition with high heat conductivity, such as copper or aluminum.

In certain embodiments of the cooling system, the system further comprising a control unit configured and operable to provide automatic control of the operation of said vacuum generator.

In certain embodiments the vacuum generator is a diaphragm vacuum pump.

In certain embodiments of the cooling system, the system comprises plurality of cooling interfaces.

In certain embodiments of the cooling system, the vacuum generator is connectable to an external power source.

In specific embodiments of the cooling system, the vacuum generator is configured to operate with a portable battery.

In certain embodiments, the cooling system, the system further comprises at least one of the following components: (a) orifice(s) for assisting in creating vacuum condition within the cooling interface; (b) a reservoir in which cooled coolant accumulates before being returned into the cooling zone; (c) splitter(s) for splitting the coolant and vacuum efficiently between parallel cooling interfaces; (d) coolant pipes in which said coolant flows. Such coolant pipes may be flexible and made of any desired material, such as plastic, rubber, silicone, polyurethane, or metal; (e) power wires; (f) user interface for displaying and controlling the temperature at the cooling interface(s) and/or the surroundings. Such user interface may be any screen, such as a computer screen, a tablet or a smart phone, or a screen attached to the system or the container being cooled; (g) a temperature sensor, e.g. a thermocouple, which may transmit data to a control unit to enable automatically activating said cooling system only when the temperature of the entity reaches a predefined temperature or when the temperature of the environment rises to a predefined temperature; (h) a transmitter for transmitting data, such as temperature, to a remote computer or smart phone, either constantly or periodically; and (i) a processor and memory.

In specific embodiments of the cooling system, the system is configured as a portable unit, in which case the rest of the system's components may reside, e.g., in a carry-on or a backpack, and the system may be powered by batteries. Alternatively, the cooling device is not portable, in which case the rest of the system's components may reside in a nearby constellation/device and powered by the main power grid.

In specific embodiments of the cooling system, the system is configured to be wearable by a subject for cooling at least a part thereof in the vicinity of the cooling interface.

In specific embodiments of the cooling system, the entity to be cooled is selected from: CPU, GPU, or any other electronic component which generates heat; a computer or any other electronic device that generates heat; body organs; pharmaceuticals; a human body; and a carrying box or a cooler.

The cooling system may further comprise pump or pumps that may assist in flowing the coolant and/or vapors in the system, as well as a filter or filtration subsystem that allows filtration of the coolant and thus prevent clogging of the system.

In another aspect of the invention, it provides a system comprising an entity to be cooled associated with the above-described thermal management system, said entity to be cooled comprising: CPU, GPU, or any other electronic component which generates heat; a computer or any other electronic device that generates heat; pharmaceuticals; human organs.

The entity to be cooled (e.g. an electronic component) may be in direct contact with the coolant. The coolant may be transferred from liquid to gas phase while directly contacting the electronic component. For example, the technique of the invention can be used for direct die (silicon) cooling, where there is no spreader in the cooling interface and the coolant evaporates in direct contact with the heat emitting entity. In this case, the cooling interface includes at least part of the heat emitting entity (i.e. entity to be cooled), and the cooling interface is sealed so when vacuum is applied by the vacuum generator, thus the coolant being in physical contact with such entity evaporates and thus absorbs its heat.

Another aspect of the present disclosure provides a method for cooling an entity comprising providing a coolant in a closed loop flow line; controllable applying partial vacuum, in a cooling zone, on a portion of said coolant to induce evaporation thereof; differentiating the pressure along said closed loop flow line to define a condensation zone, thereby allowing vapored coolant to flow downstream said condensation zone differentiated in pressure from the cooling zone, condensing said vapored coolant in the condensation zone to a liquid phase; and allowing said condensed coolant liquid to flow back to said cooling zone.

In certain embodiments of the method for cooling an entity, the condensation is obtained by exposing the vapored coolant to the surrounding pressure.

In some specific embodiments of the method for cooling an entity, the condensation is provided by condensing the vapored coolant to a pressure greater than the surrounding pressure.

In some embodiments of the method for cooling an entity, the pressure differentiation is provided by at least one of the following by orifices, one-directional valves or by varying cross section(s) along the closed loop flow line.

In certain embodiments of the method for cooling an entity, the method further comprising monitoring the temperature of said entity to be cooled and applying the vacuum controllably, e.g. activating and deactivating the vacuum generator to obtain a desired range of temperatures.

In some embodiments of the method for cooling an entity, the entity to be cooled is selected from: an electronic component; an electronic device; a cooler; an organ; a pharmaceutical; and a subject's body.

The present invention also provides a liquid flow line for use in cooling systems for controlling a liquid flow rate profile, the flow line comprising a flow restricting device located in at least a part of the flow line, said flow restricting device comprising: a hollow body configured to allow a flow of liquid through an inner cavity thereof between an inlet and an outlet of the body, said hollow body having predetermined shape and geometry of the inner cavity thereof through which the liquid flows, and an arrangement of at least two fins projecting from an inner surface of the body for affecting the flow of the liquid and obtaining a turbulent flow thereof in the interior of the body, said predetermined shape and geometry of the inner cavity and said arrangement of the at least two fins being selected to provide a desired level of turbulence and a desired flow rate profile.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3C and 3D show two examples of the restriction mechanism formed by the specific configuration of an inner cavity of the part of the flow line.

FIGS. 5A-5C are non-limiting examples of three applications, respectively, of the cooling system of the invention, wherein FIG. 5A shows how the cooling system is used for cooling an electronic device such as a computer; FIG. 5B shows the cooling system configured as a portable cooler; and FIG. 5C illustrates the cooling system configured for cooling of a human body.

DETAILED DESCRIPTION OF EMBODIMENTS

This is to describe in more details examples of a thermal management system of the invention, in particular a vacuum based closed loop cooling system for cooling an entity.

Figure 1:
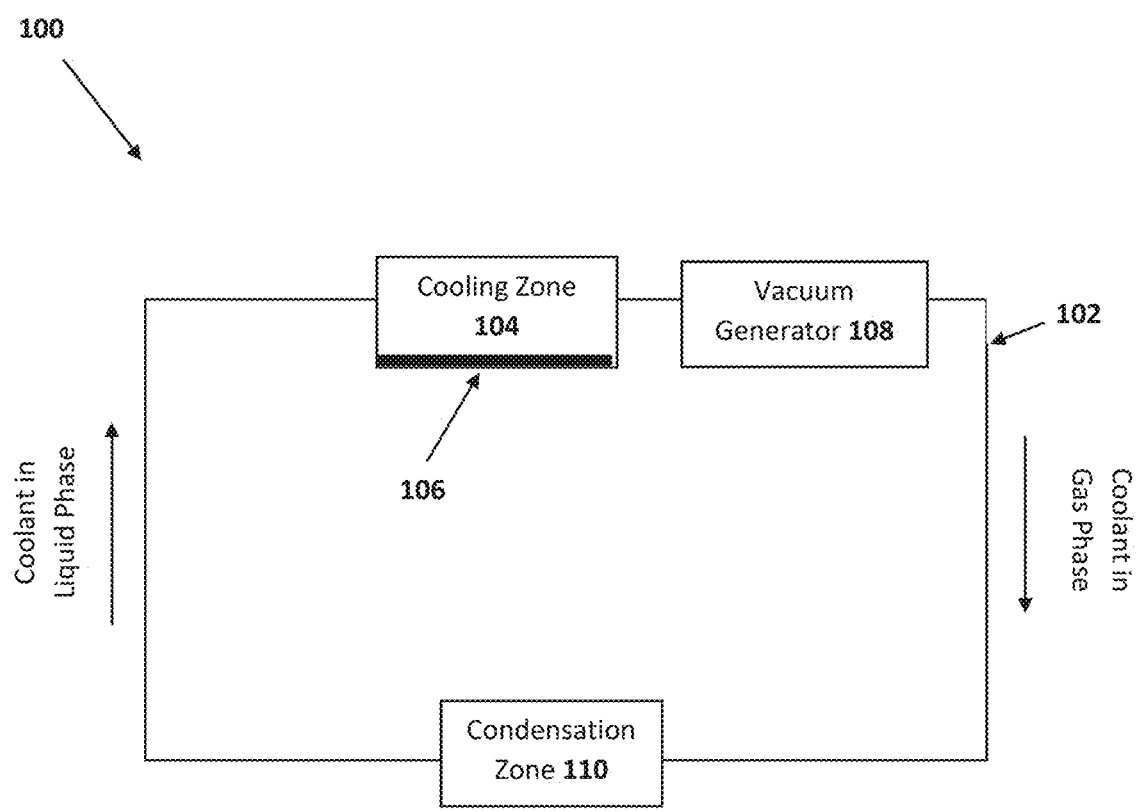
FIG. 1 shows a block diagram of the basic functional components of the cooling system of the invention.

Referring to FIG. 1, it shows, by way of a block diagram, a cooling system 100 having a flow line 102 partially or fully filled with a coolant or cooling agent. The flow line 102 may be formed by any known suitable elements/structure for allowing liquid and gas (e.g. the coolant in its liquid and gas phases) to flow along a closed loop path. Such a flow line may be formed by pipes or any other hollow cavities known in the art. The system 100 includes a cooling zone 104 in a region of the flow line arranged such that a coolant enters said cooling region while in its liquid phase and emerges said region and flows downstream in its gas phase towards a condensation zone/region 110.

The cooling zone may be in the form of a chamber (i.e. physical element having a cavity), or in a form of a region of the flow line (e.g. pipe), allowing a flow of a coolant therethrough. The cooling zone 104 defines/has one or more cooling interfaces, one such cooling interface 106 being shown in this schematic illustration, by which the cooling zone faces the entity to be cooled. In some embodiments, one or more of the structural borders of the cooling zone may serve as a cooling interface 106, such that it is in thermal contact with the entity to be cooled, directly or indirectly. The cooling zone is connected to a vacuum generator 108 in a way permitting the vacuum generator 108 to create and maintain/control vacuum conditions in the cooling zone 104.

It should be understood that the term "vacuum generator" used herein refers to any device that generates/induces vacuum through an active effect, e.g. a vacuum pump. A specific, but not limiting, example of a vacuum pump is a diaphragm vacuum pump, because the diaphragm provides a required resistant to a penetration of liquid therein. The term "vacuum conditions" as used herein refers to a pressure lower than the surrounding environment, usually lower than 1 atm. The pressure may also be lower than 0.9 atm, lower than 0.8 atm, lower than 0.7 atm, lower than 0.6 atm lower than 0.5 atm, lower than 0.4 atm, lower than 0.3 atm, lower than 0.2 atm, or lower than 0.1 atm.

The coolant is spread in the system and may be in a liquid phase or a gas phase. The coolant enters the cooling zone 104 in its liquid phase, while being exposed to vacuum conditions in the cooling zone. In said conditions, the liquid coolant boils at a relatively low temperature, i.e. a temperature lower than the boiling temperature of said coolant under atmospheric pressure. Accordingly, the coolant is transitioned into its gas phase while absorbing heat at the cooling zone 104, namely absorbing the thermal energy from the entity at the interface 106 of the cooling zone 104 (either being in direct contact with the cooling interface 106 or located in the vicinity of said interface). As previously described, the cooling interface 106 is defined by at least one of the cooling zone's borders, e.g. one or more of the inner walls of the chamber or that/those of the respective region of the flow line.

The coolant or cooling agent is selected such that it vaporizes at a relatively low pressure of e.g. less than 1 atm. (from about 0 atm. to about 1 atm.; from about 0 atm. to about 0.8 atm.; from about 0 atm. to about 0.5 atm.; from about 0 atm. to about 0.3 atm.; or about 0.3 atm.), in a relatively low temperature (in a pressure of 1 atm.) of e.g. not exceeding 40° C. (from about 0° C. to about 30° C.; from about 0° C. to about 20° C.; from about 0° C. to about 10° C.; from about 5° C. to about 25° C.; from about 10° C. to about 25° C.; from about 15° C. to about 25° C.; or from about 5° C. to about 20° C.). Examples of suitable coolants with such characteristics are Novec 7000 or C5F12, but it should be understood that the invention is not limited to any specific coolant.

The term "about" as used throughout the application means that a value noted subsequent to the term should be considered to be in a range covering values of up to 10% above and under the noted value.

The term "cooling interface" as used throughout the application refers to any element/surface that absorbs heat from an entity to be cooled. The entity to be cooled may for example be an electronic component, a human body, the air in a room or closed container, etc. Such a cooling interface (element/surface) may be in direct contact with such an entity or indirect contact therewith, e.g. via an interface or mediator or other heat conducting method, such as cooling pipes. Considering the flow line as a pipe assembly, the cooling interface may be constituted by a heat absorber coating on a portion/region of the pipe within the cooling zone.

The boiled coolant in its gas phase is flowing downstream the flow line 102 towards a condensation zone 110, which is defined by a pressure difference in said zone as compared to that of the cooling zone: the pressure in the condensation zone is higher than in the cooling zone. The condensation zone may be passive, meaning that the condensation zone 110 is under atmospheric pressure condition, namely the surrounding pressure, or a pressure below it, as long as the condensation zone 110 is under higher pressure than the cooling zone 104.

The term "surrounding pressure" throughout the application refers to the pressure level external to the system (typically ambient pressure), normally about 1 atm.

The pressure difference between the vacuum conditions in the cooling zone and the pressure in the condensation zone may be obtained by any known suitable flow restriction mechanism. This can be achieved by using variation of the cross-section of the flow line 102 in the different regions thereof, or using additional elements such as orifice(s), one-directional valve(s), etc.

The condensation zone 110 also may be active, namely pressurized zone achieved by a condenser.

The coolant is condensed to its liquid phase within the condensation zone 110, emitting the previously absorbed heat into the surrounding or through a heat exchanger (e.g. Plates Heat Exchanger). The condensation zone may be configured to be of relatively high heat conductivity to thereby emit efficiently the absorbed heat. In order to speed up the heat exchange in the condensation zone 110, a fan or any other cooling assembly may be applied to remove the heat being emitted in the condensation zone 110 from the vicinity of the condensation zone, i.e. to remove heated air. Such cooling assembly may be a part of the cooling system 100 and for example can be fixed to the flow line in or near to the condensation zone 110, or may be removably attachable thereto. The coolant then further flows, and in some embodiments may optionally be stored in a reservoir 111, as exemplified in FIG. 2, prior to the entrance back to the cooling zone 104 to start a new cycle.

Figure 2:
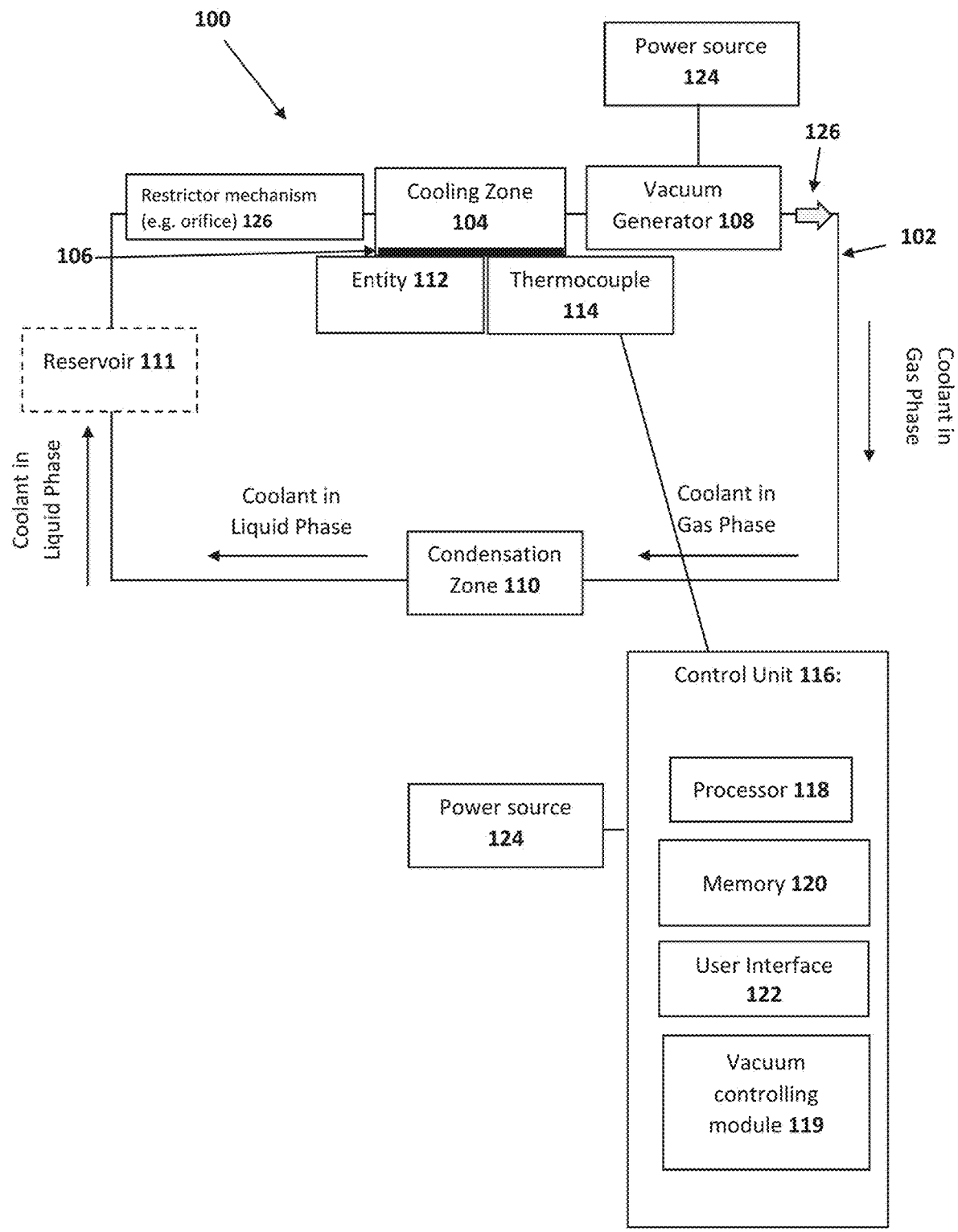
FIG. 2 shows a more detailed structure of the cooling system.

A more detailed embodiment of the cooling system 100 is exemplified in FIG. 2. To facilitate understanding, the same reference numbers are used for identifying the components common in all the examples. Thus, in this example, the cooling system 100 includes a closed loop flow line for flowing the coolant therethrough while allowing its transition between its liquid and gas phase; and cooling and condensation zones 104 and 110 arranged in a spaced-apart relationship along the flow line; and a vacuum generator 108 associated with the cooling zone 104.

The cooling interface 106 in this non limiting example is in direct contact with the entity 112 to be cooled. The entity that needs to be cooled can be, in non-limiting example, selected from: CPU, GPU, a subject's (human) body, body organs, tissues and different pharmaceuticals. The entity 112 can be also in direct contact with the coolant, such that the coolant evaporates thereon, namely the coolant changes its phase from liquid to gas while directly contacting the entity 112 being cooled. In a specific embodiment, the entity 112 that is in direct contact with the coolant liquid is an electronic component such as a CPU or a silicon chip.

Figure 6:
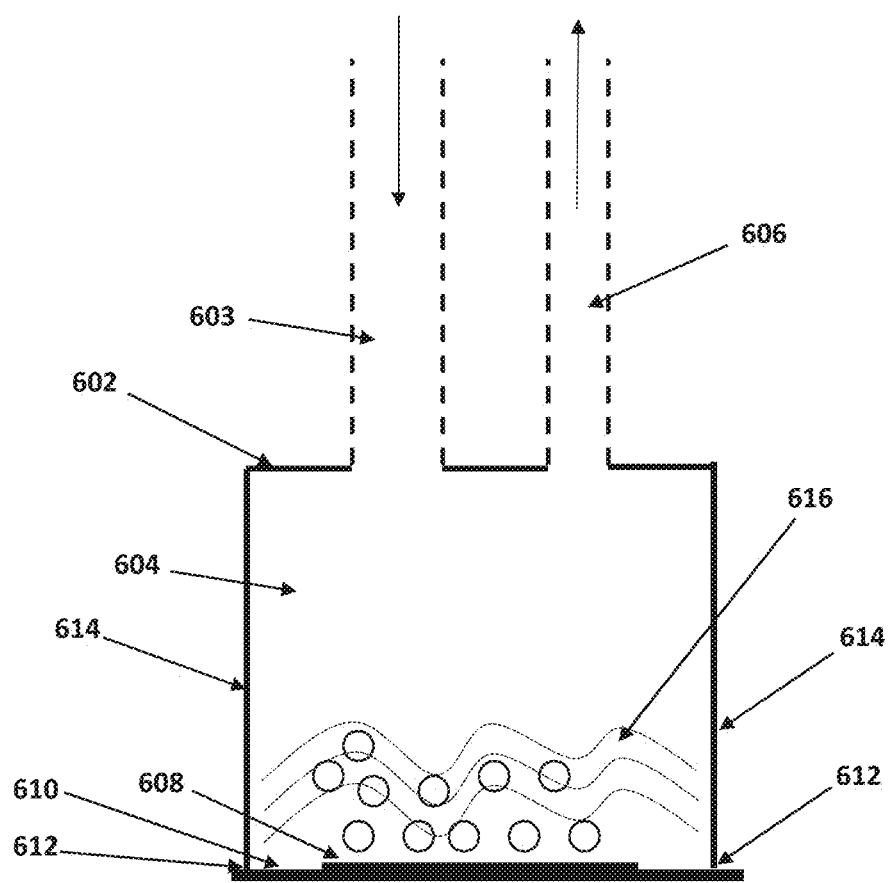
FIG. 6 is a longitudinal cross-section illustration of a non-limiting example of a cooling zone in a form of a container with no bottom separator, serves as sealing, capping at least a portion of an electronic component to be cooled, so that the coolant is in direct contact with the component.

This is exemplified in FIG. 6, which shows a cooling zone 604, defined by the inside of a sealed container 602. The container 602 has walls 614, and has a liquid inlet 603 and a gas outlet 606 fluidically connected with the cooling zone 604 inside the container 602 to allow ingress of liquid coolant into the cooling zone 604 and egress of coolant vapor out of the cooling zone 604. The sealed container 602 serves as a sealed cap or sealed cover for a portion of an electronic component 608 that needs to be cooled, such as a silicon die, located on a substrate 610. The container 602 is provided with a sealing element 612 within the contact area between the substrate 610 and the container's walls 614 to allow creation of vacuum or partial vacuum within the inside region of the container 602, i.e. in the cooling zone. Coolant 616 that is introduced into the container 602 (cooling zone 604) through the liquid inlet 604, contacts directly the electronic component, absorbs its heat until it evaporates and egresses the container via the gas outlet 606. It should be noted that the principles of the invention allows the cooling system implementation in a very small unit and using a relatively low working pressure, which allows the system to be used as on-silicon cooler (generally, on-chip cooler).

Now referring back to FIG. 2, the temperature of the entity 112 and/or the temperature of the cooling interface 106 may be measured/monitored by a temperature sensor 114, such as thermocouple. The thermocouple 114 is connected (via wires or wireless signal transmission in a well-known manner) to a control unit 116. The latter may be part of the system or may be an external device (computer), in which case the system 100 has an appropriate transmitter for transmitting data (e.g. temperature conditions) to the remote control unit.

The control unit 116 is typically a computer/electronic device including inter alia a memory 120, a user interface 122, a data processor 118, as well as data input and output utilities. In some embodiments, the control unit 116 may also include a vacuum controller 119 configured and operable for activating and deactivating the operation of the vacuum generator 108 in order to achieve and maintain the desired temperature of the entity 112 and/or the environment conditions. To this end, the temperature conditions in the vicinity of the cooling interface (as described above) are monitored, and this data is used by the processor to operate the vacuum controller 119. Thus, the operation of the vacuum generator may be managed in accordance with the data provided by the thermocouple 114 or any other sensor, to maintain the entity 112 in a desired range of temperatures. The range of temperatures that may be obtained by the cooling system of the present invention may vary from about −20° C. to about 40° C., e.g. −20° C. to about 30° C., −20° C. to about 25° C., from about −15° C. to about 20° C., from about −10° C. to about 20° C., from about −5° C. to about 20° C., from about 0° C. to about 20° C., from about 0° C. to about 15° C., from about −5° C. to about 15° C., from about −5° C. to about 10° C., from about −5° C. to about 5° C., or higher temperatures such as from 40° C. to about 50° C.

The operation of the vacuum generator 108 may be in a concomitant commands of increasing work load and/or activating an additional parallel cooling interface as will be also described below. It is to mention that the cooling system 100 is functioning and cooling also during the time slots when the vacuum generator is deactivated, though in less efficiency. A power source 124 is supplying power to the control unit 116. The power to the system may be supplied by an external power source, namely connected directly to the main power grid or by using a battery, namely portable power source. The power source 124 of the control unit 116 may also serve as a power source for the vacuum generator 108, or the vacuum generator may be associated with its own power supply (not shown here).

The cooling system 100 is differentiated in pressure along different zones of the flow line 102. In other words, the functionally different zones (cooling and condensation zones) are defined by regions of different pressure along the flow line. The pressure differentiation may be obtained by a flow restriction mechanism, defined by a geometry/shape of the closed loop flow line (or at least a portion thereof), such as varying cross section(s) along the closed loop flow line creating flow restriction zones and/or curvilinear geometry of the inner cavity of the flow line; or may be obtained by provision of restriction elements (physical elements).

A restriction element may be for example a one-directional valve, an orifice(s) or a hollow body having a varying cross section configured to create a turbulent flow. In this specific non limiting example, the restriction mechanism is constituted by restriction elements 126 in the form of valves located downstream of the cooling zone 104 and upstream of the condensation zone 110 and can be located anywhere along this path. In some other embodiments, supplemental restriction elements 126 can be located along the flow line to obtain pressure differentiation or for other purpose such as flow control of the coolant. In this example, such supplemental elements 128 (e.g. an orifice) are located between the condensation and cooling zones, so as to be upstream of the cooling zone 104 and downstream of the condensation zone 110, to maintain pressure difference between the condensation and cooling zones, and to control the flow of the coolant.

Figure 3A:
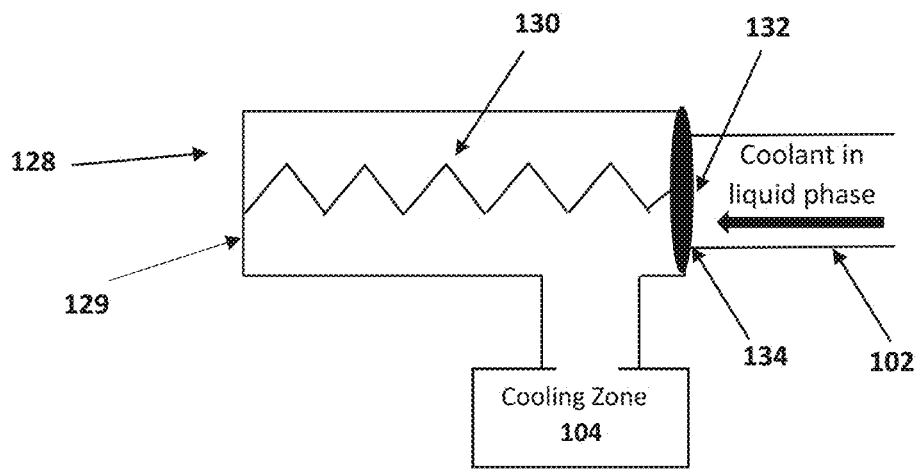
FIGS. 3A-3D show several examples of a restriction mechanism used in the flow line of the cooling system, wherein FIGS. 3A and 3B exemplify an orifice-based restriction mechanism (FIG. 3A exemplifies the restriction mechanism in its operative state, non-permitting the coolant flow, and FIG. 3B exemplifies the restriction mechanism in an inoperative state permitting the coolant flow)
Figure 3B:
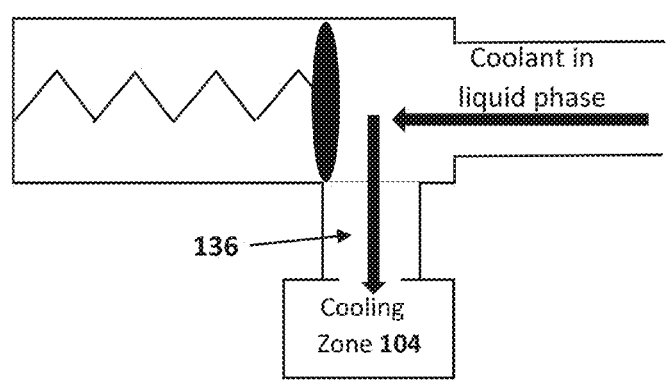

Examples for such restriction mechanisms/assemblies 128 are more specifically exemplified in FIGS. 3A-3D. The first possible example of the restriction assembly is exemplified in FIGS. 3A-3B. The restriction assembly 128 comprises a support unit 129 and a sealing element 132 displaceable between its operative extracted position being at the inlet 134 of the unit 129 in which it restricts the coolant flow towards the cooling zone, and its inoperative/retracted position in which it does not affect the coolant flow to the cooling zone. To this end, the assembly 128 includes a spring 130 which by its one end is fixed to the support unit 129 and is by its opposite end attached to the sealing element 132. The spring 130 in its loose state, as presented in FIG. 3A, is maintaining the sealing element 132 tighten to the inlet 134 not allowing the coolant flow into the cooling zone 104. When the pressure difference between the cooling zone 104 and the upstream path of the flow line 102 is reaching a predetermined value, the spring begins to shrink, as presented in FIG. 3B and thereby allowing the coolant to flow through the inlet 134 and outlet 136 of the unit 129 into the cooling zone 104. The vapored coolant formed in the cooling zone 104 is further flowing downstream to reach the condensation zone 110 as previously described (not shown).

Figure 3C:
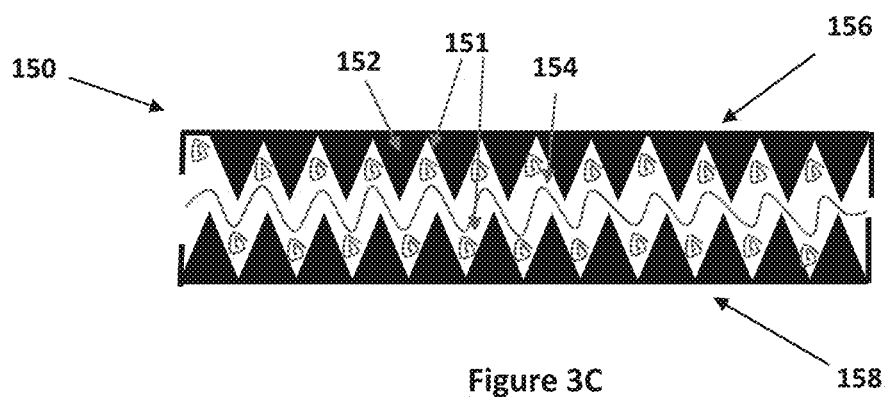
Figure 3D:
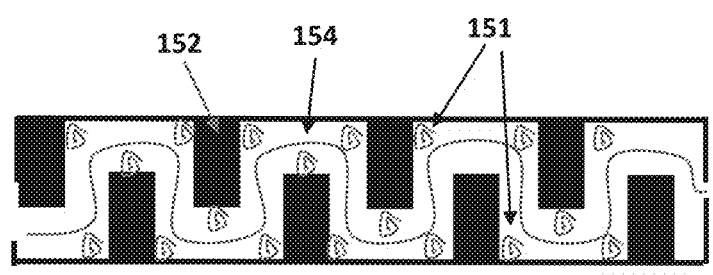

The second non-limiting example of the restriction assembly is exemplified in FIGS. 3C-3D. The restriction assembly of this specific example comprises a body 150 whose inside is configured to define a curvilinear channel/flow path between an inlet and an outlet of the body. In this specific example, this is achieved by provision of a plurality (or generally at least one) of fin(s) 152 each projecting from the inner surface/wall of the body. As shown in the figure, the restriction assembly may include an array of fins 152 arranged in a spaced-apart relationship along at least a portion of the body. The body 150 is typically elongated and can have any suitable cross-sectional shapes such as rectangular, oval, etc. The fins 152 may extend from opposite inner surfaces of the body, e.g. from a top surface 156 and a bottom surface 158 of the body 150, forming a "labyrinth" path for a liquid 154, e.g. a coolant, entering the body through the inlet and flowing therethrough and exiting through the outlet. Such a configuration creates a generally curvilinear flow path providing a turbulent flow of required level of turbulence 151, thus creating restriction force resisting the pressure of the coolant liquid which derives from the condensation zone 110 and slowing the flow of the liquid downstream, namely to the cooling zone 104 (not shown) according to a desired flow rate profile. The flow rate profile, for a given geometry of the flow path, can be adjusted by the shape and/or size of the fins 152 and their arrangement relatively to one another, thus creating different conditions for turbulences (levels of turbulence) having different resisting forces. The fins can be of any cross-sectional shape for example a triangular shape as exemplified in FIG. 3C or rectangular as exemplified in FIG. 3D. Furthermore, FIG. 3C and FIG. 4C exemplify two arrangements of the fins 152, wherein the fins are arranged adjacent to one another and are spaced apart from one another, respectively. The flow rate profile of the liquid 154 can also be controlled by controllably maintaining/setting the pressure difference between the condensation zone 110 and the cooling zone 104 (e.g. controlling the vacuum pump operation, and/or the condenser operation if any).

Owing to the fact that the invention utilizes relatively low working pressure of the system, the system is more flexible to the material compositions of the body 150 and the fins 152, and they can thus be made of non-rigid materials, such as plastic, polymer, silicon, but also can be made of rigid materials, such as metals to withstand higher pressure or lower maintenance.

Figure 4:
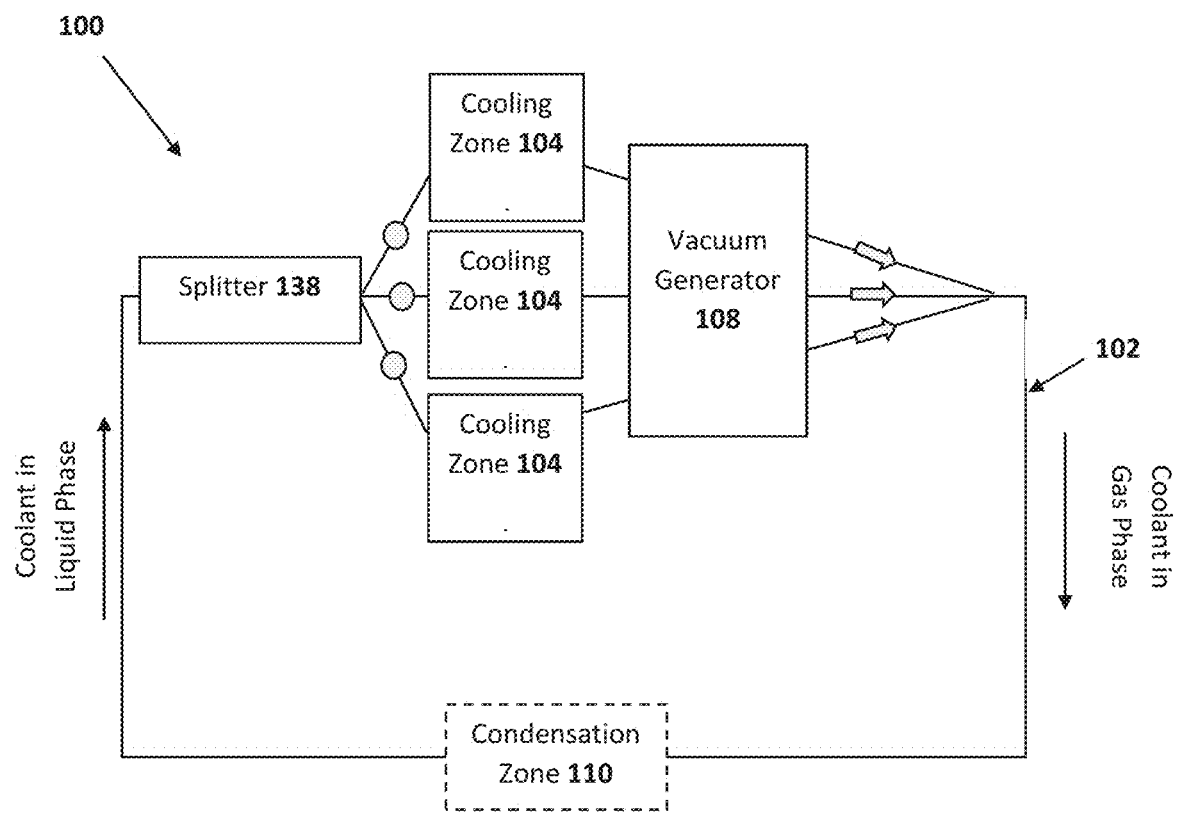
FIG. 4 is a block diagram of an example of the cooling system having more than one cooling zone.

In another embodiment of the cooling system 100, exemplified in FIG. 4, the system 100 includes a plurality (generally at least two) of cooling zones 104 having cooling interfaces 106, all associated with the common condensation zone 110. Three such cooling zones 104 are shown in this non limiting examples. It should, however, be understood that the principles of the invention are not limited to any number of the cooling zones. The liquid coolant, subsequent to the flow through the condensation zone 110, further flows through a splitter 138 that splits the liquid coolant to feed the cooling zones 104 with adequate amount of coolant while maintaining the vacuum conditions within the cooling zones 104. The splitter may be controlled (by the control unit 116) to feed the coolant selectively to only some of the cooling zones 104. Furthermore, the splitter helps to maintain the sustainability of the cooling system 100 in a case of an inactive cooling zone 104 due to malfunction or intended inactivation.

The following are some specific but not limiting examples of how the cooling system of the invention can be used for cooling various entities.

Figure 5A:
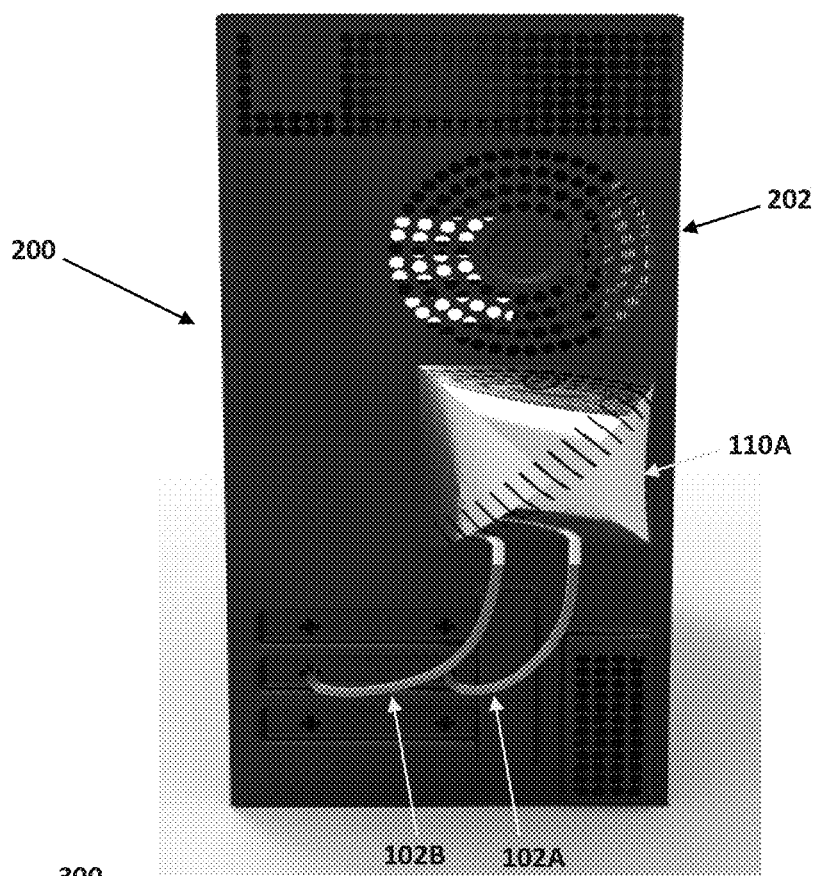

FIG. 5A illustrates the use of the above-described cooling system to cool down a computer or a heat-generating component therein. FIG. 5A shows the back-side of a computer 200 with a standard ventilator 202 mounted thereon. The cooling system is partially mounted inside the computer (and is therefore not seen in the figure) such that the cooling interface(s) is/are located in the vicinity (close contact with) heat-generating component(s) such as CPU or GPU. Two portions of the coolant pipes 102A and 102B (forming the closed loop flow line 102 described above) are shown, one leading liquid coolant to the cooling interface inside the computer, and one leading coolant vapor from the cooling interface to the condenser region 110A located outside the computer, forming an outer part of the cooling system 100. The flexibility of the pipes enables the location of said outer part at any location and orientation, thereby providing endless assembly configurations of the cooling system 100 with the computer.

Figure 5B:
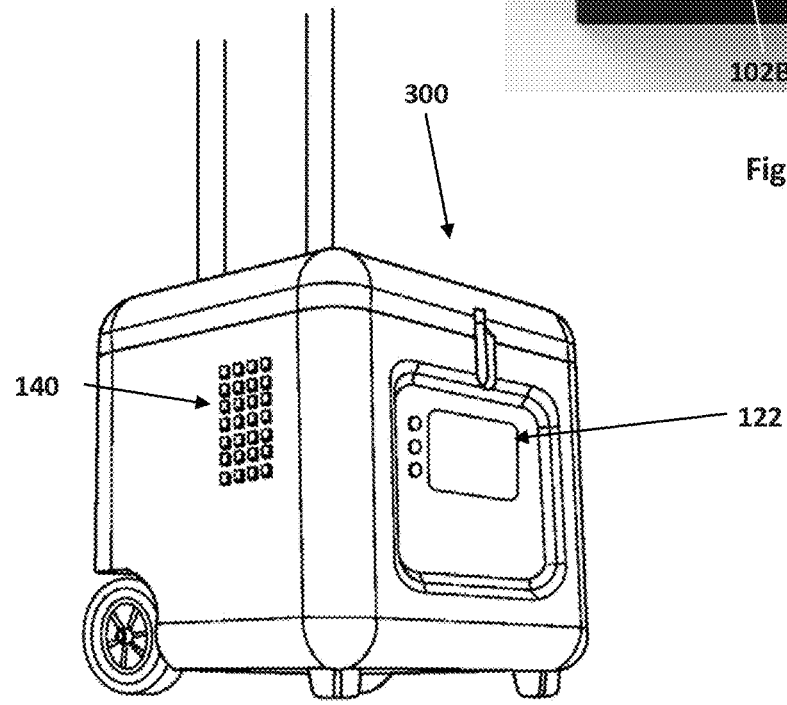

As illustrated in FIG. 5B, the cooling system of the invention may be used to cool down a cooler 300 or a delivery box for chilling different entities stored therein. FIG. 5B shows a user interface 122 of the cooling system (the control unit) located at the exterior section(s) of the cooler. The user interface may typically include a screen (e.g. an LCD screen) and operation buttons for operation of the cooling system (e.g. activating/deactivating the cooling system). In this configuration, all the components of the cooling system are located within the cooler, such that the cooling interface(s) absorb(s) heat from the inner space of the cooler thereby cooling its interior. The absorbed heat is then transferred out through dedicated venting perforations 140.

Figure 5C:
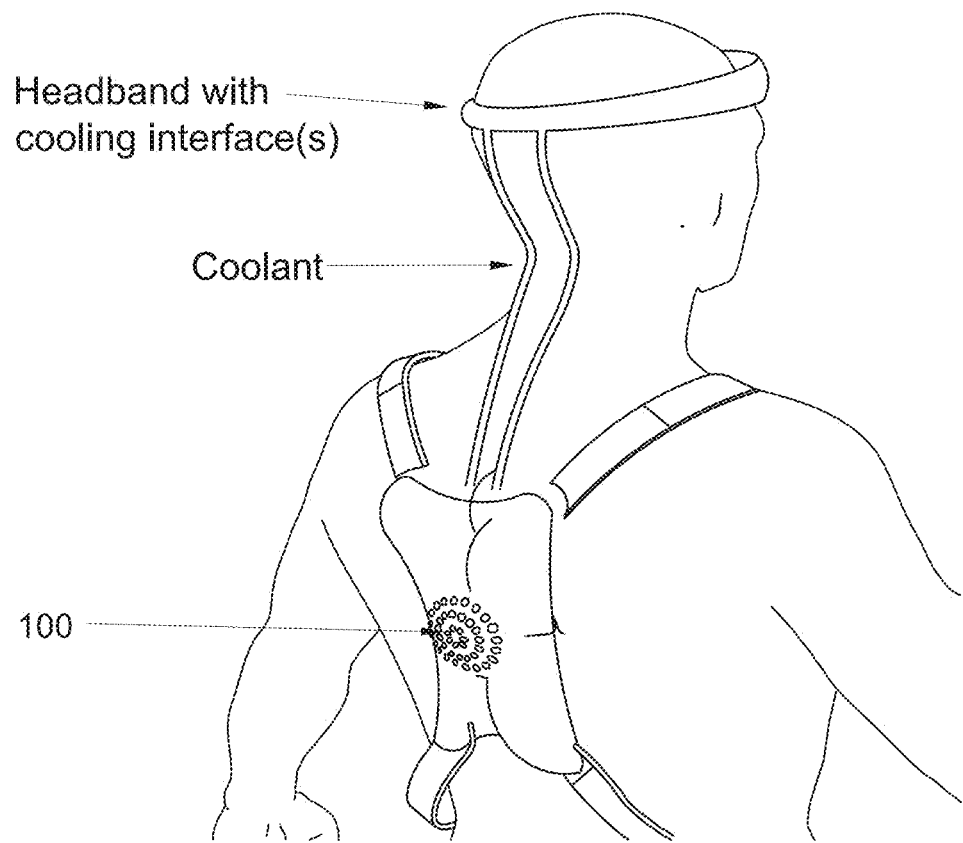

As illustrated in FIG. 5C, the cooling system may be used to cool down body temperatures, e.g. during training or surgery. FIG. 5C shows that the cooling system 100 can be portable to be worn by individual. To this end, the system uses batteries as a power source. As seen in FIG. 5C, the cooling interface(s) is/are hold in a desired location on the user's head by a dedicated strap, wherein said cooling interface(s) may be integrated inside said strap or just held by it. The cooling interface(s) may be in direct contact with the skin, or via an intermediate medium. Two coolant pipes are shown for, respectively, leading liquid coolant to the cooling interface(s) around the user's head and leading coolant vapor from said cooling interface(s) to the condenser region e.g. located in the backpack carried by the user. It is to be noted that the cooling interface may be placed on the forehead, chest, arms, legs, and/or any other organ of the subject to be cooled. The flexibility of the pipes enables the free movement of the user's head, thereby providing maximum comfort thereof. It should be noted that such a portable cooling system 100 is designed to be sufficiently light to be worn by the user so that it can be used comfortably by, e.g., soldiers, hikers, sportsman, or any other person that works under heat or strain conditions.

Thus, the present invention provides a novel approach for quick and effective cooling of various entities using a relatively simple system configuration. Those skilled in the art will readily appreciate that various modifications and changes can be applied to the above described embodiments of the invention without departing from its scope defined in and by the appended claims.

The invention claimed is:

1. A system for cooling, comprising:
   a closed loop fluid flow line configured to direct a coolant, wherein said closed loop fluid flow line comprises at least one cooling zone, a vacuum generator, and a condensation zone;
   an entity to be cooled, wherein said at least one cooling zone is adjacent to said entity, and wherein said at least one cooling zone is configured to (i) absorb thermal energy by conduction from said entity and (ii) evaporate said coolant from a liquid phase to a gas phase, thereby cooling said entity; and
   at least one restriction mechanism that is configured to provide a pressure difference between different zones along said closed loop fluid flow line to allow absorption of heat through evaporation of the coolant by applying partial vacuum, and emission of heat in different locations, having higher pressure, along the flow line,
   wherein:
   said at least one restriction mechanism is located downstream of the cooling zone and upstream of the condensation zone,
   said vacuum generator is configured to maintain a vacuum condition in said at least one cooling zone to reduce an evaporation temperature of said coolant in said at least one cooling zone,
   said condensation zone is spaced apart from and downstream of said at least one cooling zone and configured to condense said coolant from said gas phase to said liquid phase, wherein subsequent to condensation, said coolant is directed to said at least one cooling zone, and
   the pressure in said condensation zone is higher than the pressure in said at least one cooling zone.

2. The system of claim 1, wherein said at least one restriction mechanism comprises one or more members selected from the group consisting of an orifice, a one-directional valve, and a hollow body with a varied cross section configured to generate a turbulent flow.

3. The system of claim 1, wherein said at least one restriction mechanism comprises a body defining a fluid flow path, and wherein said body is configured to provide a curvilinear flow profile of said coolant along said fluid flow path.

4. The system of claim 1, wherein said at least one restriction mechanism comprises a body defining a fluid flow path, wherein said body comprises one or more fins projecting from an inner wall of said body, and wherein said one or more fins are configured to provide turbulent flow of said coolant along at least a portion of said fluid flow path.

5. The system of claim 1, wherein said at least one restriction mechanism is configured to reduce a pressure of said coolant such that said pressure of said coolant entering said at least one restriction mechanism is higher than said pressure of said coolant exiting said at least one restriction mechanism.

6. The system of claim 1, wherein said at least one cooling zone comprises at least one cooling interface that is in direct contact with said entity.

7. The system of claim 6, wherein said at least one cooling interface is a plurality of cooling interfaces.

8. The system of claim 1, wherein said coolant directly contacts said entity.

9. The system of claim 1, wherein said condensation zone comprises a region of said closed loop fluid flow line having a surrounding pressure.

10. The system of claim 1, wherein said condensation zone comprises a condenser unit configured to provide a pressure in said condensation zone above a surrounding pressure.

11. The system of claim 1, further comprising a control unit configured to (i) monitor a temperature of said entity and (ii) direct said vacuum generator to apply said vacuum condition at a pressure that is selected to control said temperature of said entity.

12. The system of claim 1, wherein said system is configured to be attached to said entity.

13. The system of claim 1, wherein said entity is an electronic component.

14. The system of claim 13, wherein said electronic component is in direct contact with said coolant.

15. A method for cooling, comprising
(a) providing a coolant in a closed loop fluid flow line as defined in claim 1, wherein said closed loop fluid flow line comprises at least one cooling zone, a vacuum generator unit, and a condensation zone, wherein said at least one cooling zone is adjacent to an entity to be cooled;
(b) using said at least one cooling zone to (i) absorb thermal energy by conduction from said entity and (ii) evaporate said coolant from a liquid phase to a gas phase, thereby cooling said entity;
(c) using said vacuum generator unit to maintain a vacuum condition in said at least one cooling zone to reduce an evaporation temperature of said coolant in said at least one cooling zone; and
(d) using said condensation zone that is spaced apart from and downstream of said at least one cooling zone to condense said coolant from said gas phase to said liquid phase, wherein subsequent to condensation, said coolant is directed to said at least one cooling zone.

16. The method of claim 15, wherein said entity is in direct contact with said coolant.

17. The method of claim 15, wherein in said condensation zone, said coolant is subjected to a pressure greater than a surrounding pressure to condense said coolant.

18. The method of claim 15, wherein in said condensation zone, said coolant IS subjected to a surrounding pressure to condense said coolant.

19. The method of claim 15, further comprising monitoring a temperature of said entity and applying said vacuum condition at a pressure that is selected to control said temperature of said entity.

\* \* \* \* \*